US012364806B2

(12) United States Patent
Nicolas et al.

(10) Patent No.: US 12,364,806 B2
(45) Date of Patent: *Jul. 22, 2025

(54) HOLDING DEVICE CONFIGURED TO SUPPORT A PLURALITY OF MEDICAL CONTAINERS SUCH AS SYRINGES

(71) Applicant: Becton Dickinson France, Le Pont de Claix (FR)

(72) Inventors: Maxime Nicolas, Grenoble (FR); Julien Singer, Domene (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,994

(22) Filed: Oct. 17, 2023

(65) Prior Publication Data

US 2024/0042123 A1 Feb. 8, 2024

Related U.S. Application Data

(63) Continuation of application No. 17/698,594, filed on Mar. 18, 2022, now Pat. No. 11,819,658, which is a continuation of application No. 17/051,882, filed as application No. PCT/EP2019/060511 on Apr. 24, 2019, now Pat. No. 11,298,455.

(30) Foreign Application Priority Data

May 2, 2018 (EP) ..................................... 18305548

(51) Int. Cl.
*A61M 5/00* (2006.01)

(52) U.S. Cl.
CPC .................................. *A61M 5/008* (2013.01)

(58) Field of Classification Search
CPC .......... A61M 5/00; A61M 5/008; B01L 9/06; B65D 1/34; B65D 1/36
See application file for complete search history.

(56) References Cited

U.S. PATENT DOCUMENTS

| 8,100,263 B2 | 1/2012 | Vanderbush et al. |
| 8,800,800 B2 | 8/2014 | Gerner et al. |
| 9,095,848 B2 | 8/2015 | Carrel et al. |
| 10,023,358 B2 | 7/2018 | Carrel |

(Continued)

FOREIGN PATENT DOCUMENTS

| DE | 102011104300 A1 | 9/2012 |
| JP | 201693490 A | 5/2016 |

(Continued)

*Primary Examiner* — Bryon P Gehman
(74) *Attorney, Agent, or Firm* — The Webb Law Firm

(57) ABSTRACT

This holding device comprising a supporting plate, the supporting plate having an upper face, a lower face opposite the upper face, a plurality of openings arranged according to a predetermined pattern and each configured to receive a barrel of one of the medical containers, plurality of reinforcing ribs protruding from at least one of the upper and lower faces and extending between adjacent openings of the plurality of openings, and the plurality of reinforcing ribs comprises at least one oblique rib extending obliquely relative to a longitudinal direction of the supporting plate from one side to another side of the supporting plate and between two different pairs of adjacent peripheral openings.

13 Claims, 3 Drawing Sheets

(56) References Cited

U.S. PATENT DOCUMENTS

| | | |
|---|---|---|
| 10,143,793 B2 | 12/2018 | Gagnieux et al. |
| 10,207,832 B2 | 2/2019 | Narvekar et al. |
| 10,800,557 B2 * | 10/2020 | Narvekar ................. B01L 9/06 |
| 11,498,709 B2 | 11/2022 | Narvekar et al. |
| 2015/0089830 A1 | 4/2015 | Wissner et al. |
| 2016/0121042 A1 | 5/2016 | Christensen |
| 2019/0070357 A1 | 3/2019 | Evans et al. |
| 2021/0220547 A1 | 7/2021 | Sonoyama et al. |

FOREIGN PATENT DOCUMENTS

| | | |
|---|---|---|
| WO | 2011015896 A1 | 2/2011 |
| WO | 2012143533 A1 | 10/2012 |
| WO | 2016166765 A1 | 10/2016 |
| WO | 2017132554 A1 | 8/2017 |

\* cited by examiner

HOLDING DEVICE CONFIGURED TO SUPPORT A PLURALITY OF MEDICAL CONTAINERS SUCH AS SYRINGES

CROSS-REFERENCE TO RELATED APPLICATIONS

This application is a continuation of U.S. patent application Ser. No. 17/698,594 filed Mar. 18, 2022, which is continuation of U.S. patent application Ser. No. 17/051,882 filed Apr. 24, 2019 (now U.S. Pat. No. 11,298,455), which is the United States national phase of International Application No. PCT/EP2019/060511 filed Apr. 24, 2019, and claims priority to European Patent Application No. 18305548.2 filed May 2, 2018, the disclosures of which are hereby incorporated by reference in their entirety.

BACKGROUND OF THE INVENTION

The present invention relates to a holding device for supporting a plurality of medical containers.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a container supported by the holding device of the invention, and the "proximal direction" is to be understood as meaning the opposite direction to said direction of injection, that is to say the direction towards the user's hand holding a container as for an injection operation.

Medical containers, such as pre-fillable or prefilled syringes, often need to be transported from one site to another site, for instance from a manufacturing site to a second site where the medical containers may be filled with a pharmaceutical composition agent, such as a vaccine, a medicine or a therapeutic agent. Less frequently, the medical containers may be manufactured and filled in the same first site and then be transported to a storage site. During transportation, the medical containers are usually held by a holding device such as a nest.

A nest is a plate-shaped tray that is generally configured to support more than one hundred medical containers. The nest comprises several through-holes aligned according to predetermined rows, each hole being configured to receive one medical container. The barrel of each medical containers extends through the holes in a direction substantially orthogonal to the nest.

The nest is usually placed inside a box-shaped tub which has one opening sealed by a sealing cover. Removal of the medical containers from this tub basically requires peeling off the sealing cover, removing the nest holding the medical containers from the tub and then removing the medical containers from the nest by axially sliding the medical containers relative to the nest. Before being removed from the nest and packaged individually, the medical containers are filled with a pharmaceutical composition agent by means of a filling machine.

When handled by the filling machines, it may happen that the nests slightly deform, for example bend or warp, due to the weight of all the medical containers held by the nest. As a result, the flanges of the medical containers supported by the slightly deformed are no more positioned in a rigorously same plane, which may lead to some inaccuracy during the filling process.

Besides, even though the existing nests are enabled to concurrently support and handle a large number of medical containers, which limits the storage or transportation costs, there however remains a constant need to reduce costs.

SUMMARY OF THE INVENTION

An aspect of the invention is a holding device configured to support a plurality of medical containers, said holding device comprising: a supporting plate, said supporting structure having an upper face, a lower face opposite said upper face, a plurality of openings arranged according to a predetermined pattern and each configured to receive a barrel of one of said medical containers, a plurality of reinforcing ribs protruding from at least one of said upper and lower faces and extending between adjacent openings of said plurality of openings.

The holding device according to the invention is therefore stiffened by the presence of several reinforcing ribs. This increased stiffness prevents the supporting plate from deforming when this supporting plate is being handled by the filling machines. The accuracy of the filling process may thus be improved. Besides, due to the increased stiffness of the holding device, the thickness of the supporting plate may be reduced. As a result, the quantity of raw material necessary to manufacture the holding device may be reduced, thereby enabling to reduce costs.

The reinforcing ribs of said plurality of reinforcing ribs extend from one side to another side of the supporting plate.

By a reinforcing rib extending from one side to another side of the supporting plate it should be understood a reinforcing rib which extends at least from a row of peripheral openings to another row of peripheral openings. The peripheral openings are the outermost openings of the plurality of openings; accordingly, the peripheral openings surround the other openings of said plurality of openings. The ends of the reinforcing rib may be located between two different pairs of adjacent peripheral openings. The reinforcing rib may however further extend until a peripheral rim of the supporting plate, i.e. from a portion of said peripheral rim to another portion. In this case, the ends of the reinforcing rib are located at the peripheral rim of the supporting plate.

The reinforcing ribs extend between adjacent rows of openings. The reinforcing ribs are parallel to said adjacent rows of openings. The reinforcing ribs extend without intersecting the openings.

In an embodiment, the plurality of reinforcing ribs comprises two central ribs intersecting each other substantially at the center of the supporting plate.

In an embodiment, the plurality of reinforcing ribs comprises one or several oblique ribs extending obliquely relative to a longitudinal direction of the supporting plate.

In an embodiment, the plurality of reinforcing ribs comprises primary reinforcing ribs that are between 1.5 to 2 times thicker than the supporting plate.

This feature offers the best compromise between cost reduction and stiffness.

The thickness of a reinforcing rib is the distance between two lateral faces of this reinforcing rib, i.e. the distance measured in a direction orthogonal to a longitudinal direction of the reinforcing rib and parallel to the supporting plate.

The thickness of the supporting plate is the distance between the upper and lower faces of the supporting plate, measured in a direction orthogonal to the supporting plate.

In an embodiment, the plurality of reinforcing ribs comprises at least one secondary rib extending parallel to one of said central ribs.

In an embodiment, said at least one secondary rib is orthogonal to a longitudinal direction of the supporting plate.

In an embodiment, said at least one secondary rib is thinner than the central ribs.

In an embodiment, said at least one secondary rib is thinner than the oblique ribs.

Advantageously, the plurality of reinforcing ribs may include at least one primary reinforcing rib and at least one secondary reinforcing rib, the at least one secondary reinforcing rib being thinner than the at least one primary reinforcing ribs.

In an embodiment, at least one central reinforcing rib is between 1.5 to 2 times thicker than at least one secondary rib.

In an embodiment, at least one oblique reinforcing rib is between 1.5 to 2 times thicker than at least one secondary rib.

Advantageously, the plurality of reinforcing ribs comprises at least one longitudinal reinforcing rib extending parallel to a longitudinal direction of the supporting plate. The at least one longitudinal reinforcing rib may be one of the central reinforcing ribs. The plurality of reinforcing ribs may comprise several longitudinal reinforcing ribs, at least one of them being a primary reinforcing rib.

Advantageously, the plurality of reinforcing ribs comprises at least one transversal reinforcing rib extending parallel to a transversal direction of the supporting plate. The at least one transversal reinforcing rib may be one of the central reinforcing ribs. The plurality of reinforcing ribs may comprise several transversal reinforcing ribs, at least one of them being a primary reinforcing rib.

In an embodiment, each opening is surrounded by a chimney protruding from one of the upper or lower faces of the supporting plate so as to guide insertion of a barrel of the medical containers into said opening.

This feature allows to guide the medical containers through the supporting plate.

According to one embodiment, the chimney comprises at least two guiding tabs, a slit being delimited between said at least two guiding tabs.

This feature allows to reduce raw material costs due to the slits between the guiding tabs.

According to one embodiment, the chimney comprises four guiding tabs, a slit being delimited between two adjacent guiding tabs.

In an embodiment, said plurality of reinforcing ribs comprises one or several reinforcing ribs formed by adjacent chimneys, more precisely adjacent guiding tabs, connected to each other.

This has the advantage of further reducing raw material costs while still improving the stiffness of the supporting plate.

In an embodiment, the chimneys or the guiding tabs forming said one or several reinforcing ribs are thicker than the other chimneys or guiding tabs.

Advantageously, the guiding tabs and the reinforcing ribs protrude from the same face of the supporting plate.

In an embodiment, the height of the chimney or guiding tabs is preferably equal to the height of the reinforcing ribs.

The height of a chimney or a guiding tab is the distance between a proximal end and a distal end of the chimney or guiding tab.

In an embodiment, the supporting plate comprises a peripheral edge protruding from one of said upper and lower faces and surrounding said plurality of openings.

This improves the stiffening of the supporting plate.

In an embodiment, at least one of the reinforcing ribs has chamfered ends.

This allows reducing the raw material costs without compromising the stiffness of the supporting plate.

In an embodiment, the oblique ribs have chamfered ends.

Advantageously, the openings are arranged in staggered rows.

As a result, the openings of two adjacent rows are offset relative to each other. Having openings in quincunx relative to each other permits to support a large number of medical containers. More precisely, an opening is positioned at the center of a square formed by four adjacent openings.

Advantageously, the holding device is a nest.

A second aspect of the invention concerns an assembly configured to support a plurality of medical containers, the assembly comprising: a tub; at least one holding device according to the first aspect.

The tub may be a box-shaped housing delimiting an internal volume configured to contain the holding device and the medical containers supported by this holding device. The tub may have at least one opening configured to permit insertion of the holding device into the internal volume or removal of the holding device outside the tub. The tub may also comprise a sealing cover configured to seal the opening and which may be peeled off before removal of the holding device. The sealing cover may comprise a Tyvek® sheet or any material that is airtight but permeable to a sterilization gas such as for example ethylene oxide (EO).

Another aspect is a holding device configured to support a plurality of medical containers, said holding device comprising: a supporting plate, said supporting plate having an upper face, a lower face opposite said upper face, a plurality of openings arranged according to a predetermined pattern and each configured to receive a barrel of one of said medical containers, each opening being surrounded by at least two guiding tabs protruding from one of the upper or lower faces of the supporting plate so as to guide insertion of a barrel of the medical containers into said opening, a slit being delimited between said at least two guiding tabs.

This holding device provides a guiding of the medical containers when the medical containers are inserted or removed from the supporting plate, while reducing costs because the slits separating the guiding tabs enable to use as little raw material as possible.

This holding device may also comprise some or all of the additional features detailed in the present description.

For example, this holding device may comprise a plurality of reinforcing ribs protruding from at least one of said upper and lower faces and extending from one to another side of the supporting plate between adjacent openings of said plurality of openings.

The plurality of reinforcing ribs may comprise two central ribs intersecting each other substantially at the center of the supporting plate, and oblique ribs extending obliquely relative to said central ribs. The central and oblique reinforcing ribs may be between 1.5 to 2 times thicker than the supporting plate.

For example, said plurality of reinforcing ribs comprises one or several reinforcing ribs formed by adjacent guiding tabs connected to each other. The guiding tabs forming said one or several reinforcing ribs may be thicker than the other guiding tabs. The guiding tabs and the reinforcing ribs preferably protrude from the same face of the supporting plate. The height of the guiding tabs may be equal to or greater than the height of the reinforcing ribs.

The plurality of reinforcing ribs advantageously comprises at least one secondary rib extending parallel to one of said central ribs. Preferably, said at least one secondary rib is orthogonal to a longitudinal direction of the supporting plate. Said at least one secondary rib is advantageously thinner than the central and oblique ribs. Advantageously, the central and oblique reinforcing ribs are between 1.5 to 2 times thicker than said at least one secondary rib. Advantageously, said at least one secondary rib and the supporting plate may have a similar thickness. The reinforcing ribs preferably have chamfered ends For example, the supporting plate comprises a peripheral edge protruding from one of said upper and lower faces and surrounding said plurality of openings.

For example, the openings are arranged in staggered rows.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1:
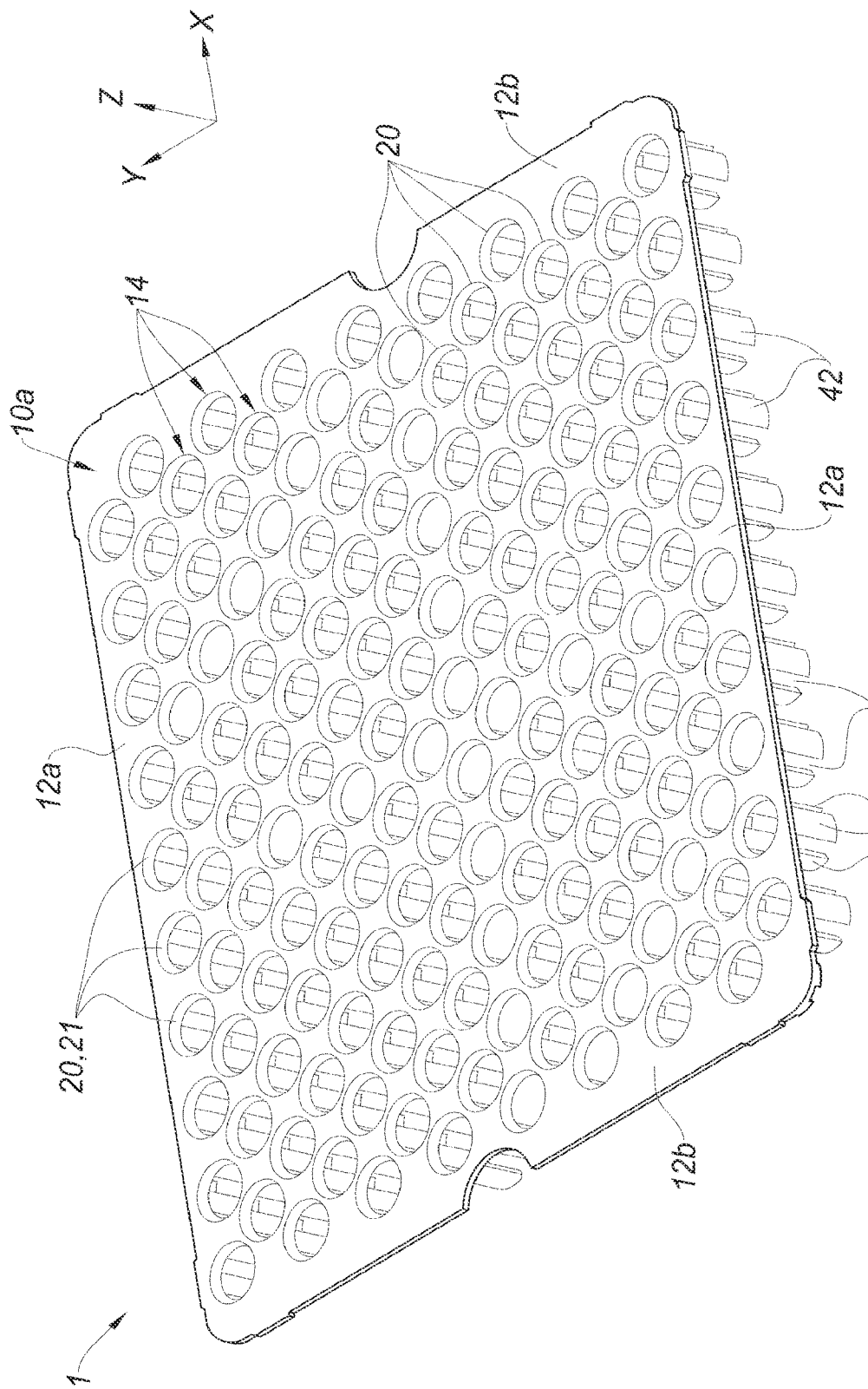
FIG. 1 is a top perspective view of a holding device according to an embodiment of the invention.

With reference to the figures is shown a holding device 1, or nest, according to an embodiment of the invention. The holding device 1 is configured to concurrently support a plurality of medical containers (not shown). The holding device 1 therefore serves as a nest for packaging, storing, transporting and handling on a filling line the medical containers. A nest is a plate provided with openings each configured to receive one medical containers and having a leaning surface so that the nest may rest on a shoulder inside a box-shaped housing or be handled by a filling machine.

It should be noted that the medical containers may be syringes, such as pre-fillable syringes. The medical containers are intended, after filling, to contain a pharmaceutical composition such as a vaccine, a medicine or a therapeutic pharmaceutical composition.

A medical container such as a syringe typically comprises an elongated barrel defining a reservoir for containing the pharmaceutical composition agent, a plunger stopper located inside the barrel, a plunger to move the plunger stopper inside the barrel and expel the pharmaceutical composition agent through a tip closed by a staked needle and/or needle shield at a distal end of the barrel, and a flange at a proximal end of the barrel. The flange provides a surface for positioning a user's fingers, generally the index and the middle fingers, while the plunger rod is activated with the thumb.

The holding device 1 comprises a supporting plate 10 configured to concurrently support the plurality of medical containers. By supporting plate it is meant a substantially plane piece having a small thickness compared to the other dimensions such as length and width.

The supporting plate 10 has an upper face 10a, a lower face 10b opposite the upper face 10a and a peripheral rim joining the upper and lower faces 10a, 10b.

The supporting plate 10 is preferably rectangular and thus defines two longitudinal sides 12a and two transversal sides 12b.

With reference to FIG. 1, the supporting plate 10 substantially extends in a plane XY that is orthogonal to a vertical direction Z. The longitudinal sides 12a extend along a longitudinal direction X orthogonal to the vertical direction Z and the transversal sides 12b extend along a transverse direction Y orthogonal to the longitudinal and vertical directions X, Z.

Figure 2:
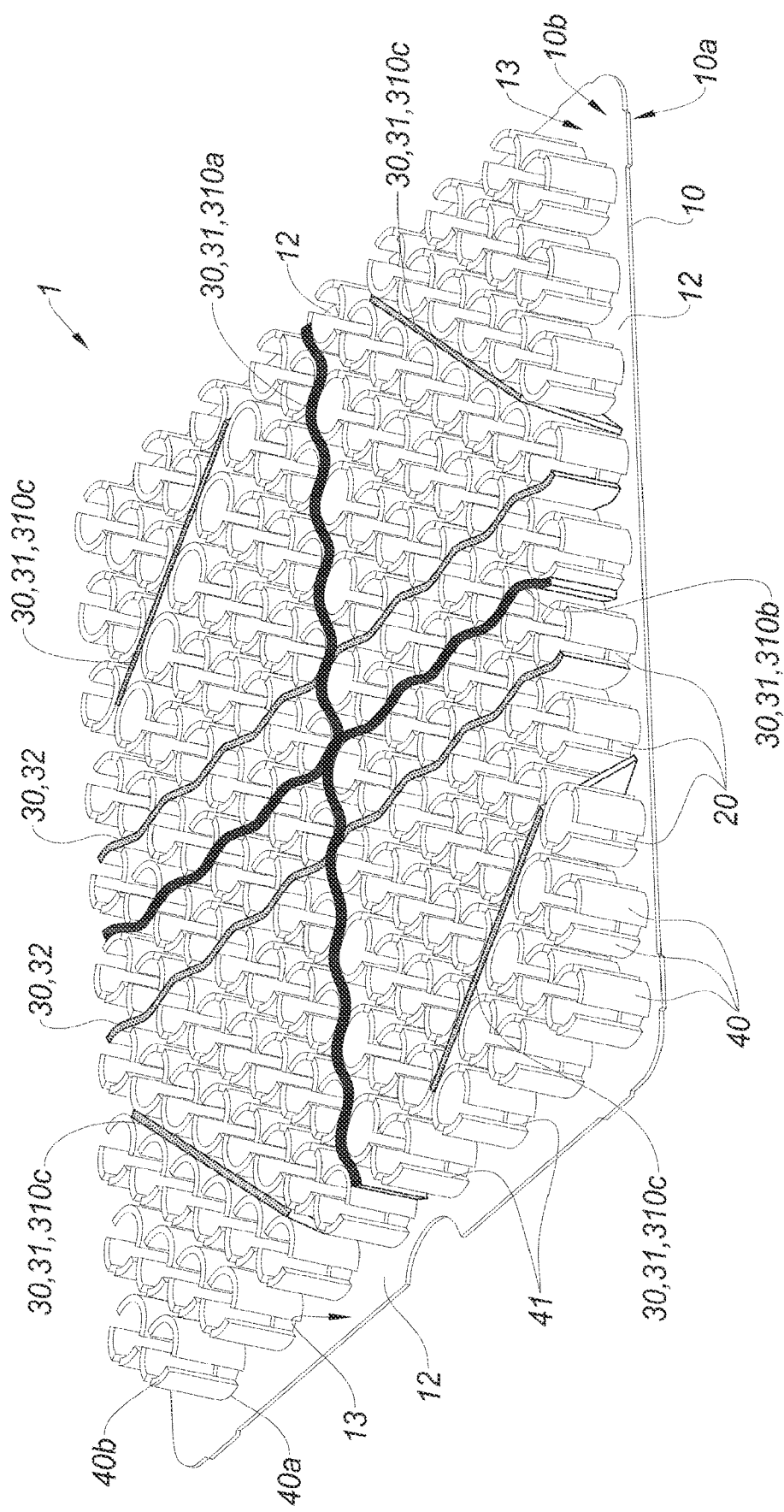
FIG. 2 is a bottom perspective view of a holding device according to an embodiment of the invention.
Figure 4:
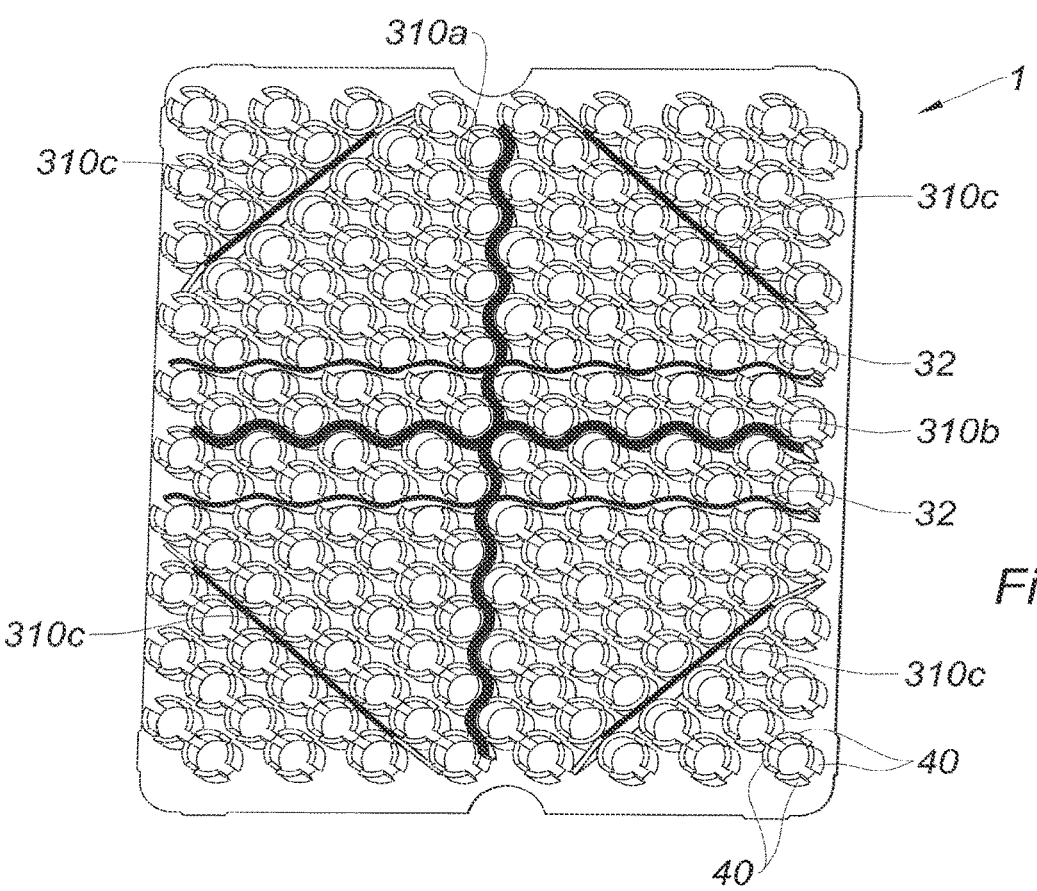
FIG. 4 is a bottom view of a holding device according to an embodiment of the invention.

With reference to FIGS. 2 and 4, the supporting plate 10 may comprise one or several leaning surfaces 13 configured to abut on a shoulder arranged inside a box-shaped housing. These leaning surfaces 13 also define handling portions of the supporting plate 10 so that the supporting plate 10 may be handled on the filling lines. The leaning surfaces 13 preferably extend on the lower face 10b. The leaning surfaces 13 also preferably extend in the transverse direction Y.

Figure 3:
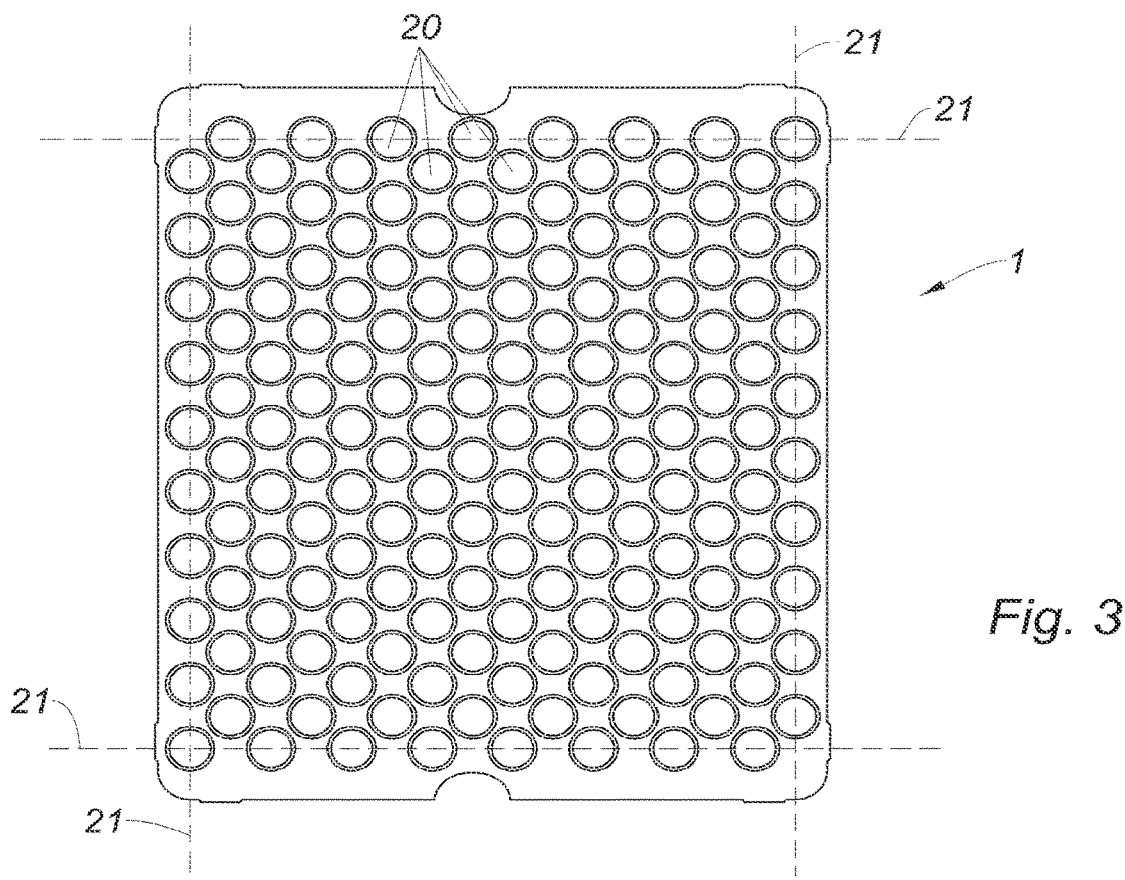
FIG. 3 is a top view of a holding device according to an embodiment of the invention.

The holding device 1 also comprises a plurality of openings 20, each of said openings 20 being configured to receive the barrel of one of the medical containers. The openings 20 are preferably circular so as to receive cylindrical barrels. As visible on FIGS. 3 and 4, the openings 20 are through-openings which extend through the plate-shaped structure 10 from the upper face 10a to the lower face 10b.

The openings 20 are arranged according to a predetermined pattern such as parallel rows which for example may be seen as extending along the longitudinal direction X or the transverse direction Y or an oblique direction with regard to the longitudinal and transverse directions X, Y. As illustrated on the Figures, the openings 20 may be arranged in staggered rows, that is to say in quincux, so that the holding device 1 may receive as much medical containers as possible.

The supporting plate 10 may comprise abutment surfaces 14 each configured to support the flange of one of the medical containers. Each abutment surface 14 preferably extends around one of the openings 20, and may be part of the upper or lower face 10a, 10b, preferably the upper face 10a as visible on FIG. 1, or which may be located at the distal end 40b of a chimney 40. The abutment surfaces 14 may have a circular shape.

With reference to FIGS. 2 and 4, the holding device 1 may comprise a plurality of reinforcing ribs 30 configured to stiffen the supporting plate 10. The reinforcing ribs 30 protrude from one of the upper or lower face 10a, 10b, preferably the lower face 10b, and longitudinally extend between adjacent openings 20.

The reinforcing ribs 30 extend between two adjacent longitudinal, transversal or oblique rows of openings 20. The reinforcing ribs 30 are parallel to said adjacent rows of openings 20. The reinforcing ribs 30 extend without intersecting the openings 20.

The reinforcing ribs 30 may be shaped as walls protruding orthogonally to the supporting plate 10. As shown on FIGS. 2 and 4, the reinforcing ribs 30 longitudinally extend along a direction orthogonal to the vertical direction Z. The reinforcing ribs 30 may be straight, or may be wavy as will be described hereinafter. Anyway, the reinforcing ribs 30 longitudinally extend along a substantially straight line.

It should be noted that the reinforcing ribs 30, preferably all the reinforcing ribs 30, extend from one side 12 to another side 12 of the supporting plate 10. More precisely, the reinforcing ribs 30 longitudinally extend at least from one peripheral row 21 to another peripheral row 21 of the plurality of openings 20. The peripheral rows 21 of openings 20 are formed by the outermost openings 22 of the plurality of openings 20. In the example shown on FIG. 3, the holding device 1 comprises four peripheral rows 21.

The reinforcing ribs 30 have two opposite ends 33 which are preferably located at two different sides 12 of the supporting plate 10. For example, each end is located between two adjacent peripheral openings 22. It should be noted that the reinforcing ribs 30 extend continously from one end to the other. As shown on FIG. 2, at least some reinforcing ribs 30 advantageously have chamfered ends. As a result, the height of these reinforcing ribs 30 decreases towards these ends.

As can be seen on FIG. 2 or 4, the plurality of reinforcing ribs 30 may include primary reinforcing ribs 31 and secondary reinforcing ribs 32, the secondary reinforcing ribs 32 being advantageously thinner than the primary reinforcing ribs 31.

The holding device 1 may comprise one or several central reinforcing ribs 310a, 310b. These central reinforcing ribs 310a, 310b cross each other substantially at the center of the supporting plate 10, as visible on FIG. 4. The central reinforcing ribs 310a, 310b may have a wavy shape. Preferably, the central reinforcing ribs 310a, 310b are perpendicular to each other.

A first central reinforcing rib 310a extends from the middle of one of the transversal sides 12b to the middle of the opposite transversal side 12b, along a direction substantially parallel to the longitudinal sides 12a of the supporting plate 10.

A second central reinforcing rib 310b extends from the middle of one of the longitudinal sides 12a to the middle of the opposite longitudinal side 12a, along a direction substantially parallel to the transversal sides 12b of the supporting plate 10.

The holding device 1 may also comprise one or several oblique reinforcing ribs 310c which extend obliquely relative to the central reinforcing ribs 310a, 310b. Preferably, the oblique reinforcing ribs 310c each extend from one of the longitudinal sides 12a to one of the transversal sides 12b. The oblique reinforcing ribs 310c may be continuous and non-segmented. Preferably, the oblique reinforcing ribs 310c are straight.

In the example shown of FIGS. 2 and 4, the holding device 1 comprises four oblique reinforcing ribs 310c. The central reinforcing ribs 310a, 310b divide the supporting plate in several areas, such as four quarters. In each of these areas extends one oblique reinforcing rib 310c.

In the embodiment illustrated on FIGS. 2 and 4, the oblique reinforcing ribs 310c have chamfered ends.

The central reinforcing ribs 310a, 310b and the oblique reinforcing ribs 310c form the primary reinforcing ribs 31. As mentioned above, the holding device 1 may further include at least one secondary reinforcing rib 32, for example two secondary reinforcing ribs 32 as illustrated on FIGS. 2 and 4. In a embodiment, the secondary reinforcing ribs 32 are advantageously parallel to one of the central reinforcing ribs 310a, 310b, for example parallel to the second central reinforcing rib 310b. Preferably, the secondary reinforcing ribs 32 extend from a longitudinal side 12a of the supporting plate 10 to the opposite longitudinal side 12a. As a result, the secondary reinforcing ribs 32 increase the stiffness of the supporting plate 10 without requiring too much raw material. The secondary reinforcing ribs 32 may be wavy, such as the central reinforcing ribs 310a, 310b. The secondary reinforcing ribs 32 may be arranged symetrically relative to one of the to one of the central reinforcing ribs 310a, 310b, for example parallel to the second central reinforcing rib 310b.

Preferably, the thickness of the main reinforcing ribs 31 is comprised between 150% and 200% of the thickness of the second reinforcing ribs 32. The thickness of the reinforcing ribs is measured in a direction orthogonal to their longitudinal direction and parallel to the horizontal plane XY. It should also be noted that the primary reinforcing ribs 31 advantageously have a thickness that is between 150% to 200% of the thickness of the supporting plate 10. The thickness of the supporting plate 10 is the distance measured in the vertical direction Z between the upper and lower faces 10a, 10b. Still advantageously, the secondary reinforcing ribs 32 and the supporting plate 10 may have a similar thickness.

For example, the plate-shaped structure 10 may have a thickness comprised between 1.3-1.5 mm, preferably 1.4 mm. The primary reinforcing ribs 31 may have a thickness comprised between 2.3-2.6 mm, for example a thickness of 2.5 mm for the central reinforcing ribs 310a, 310b and a thickness of 2.4 mm for the oblique reinforcing ribs 310c. The secondary reinforcing ribs 32 may have a thickness comprised between 1.3-1.5 mm, preferably 1.4 mm.

With reference to FIGS. 1 and 2, the holding device 1 may comprise chimneys 42, formed by guiding tabs 40, which are configured to form a guiding conduit around each opening 20 in order to guide insertion of the barrel of the medical containers into each of these openings 20.

The guiding tabs 40 protrude from one of the upper and lower faces 10a, 10b of the supporting plate 10, preferably from the lower face 10b. The guiding tabs 40 and the abutment surfaces 14 are arranged on opposite faces of the supporting plate 10.

In a preferred embodiment, the guiding tabs 40 and the reinforcing ribs 30 preferably protrude from the same face of the supporting plate 10. In a preferred embodiment, the guiding tabs 40 protrude orthogonally to the supporting plate 10, along the vertical direction Z.

The guiding tabs 40 extend around the openings 20 so that each opening is surrounded by at least two guiding tabs 40, for example four such as visible on FIG. 2. As shown on FIG. 2, each guiding tab 40 has a proximal end 40a which is secured to the supporting structure 10 and a distal end 40b opposite said proximal end 40a. The proximal end 40a extends along the periphery of one of the openings 20. The proximal end 40a and the distal end 40b may have an arcuate shape so that the guiding tabs 40 have a cylindrical shape.

As visible on FIG. 2, the guiding tabs 40 of a same opening 20 are separated by slits 41. The slits 41 may advantageously extend along a direction orthogonal to the supporting plate 10. The slits 41 preferably extend from the proximal end 40a to the distal end 40b of the guiding tabs 40.

In a preferred embodiment, the height of the reinforcing ribs 30 is equal to or lower than the height of the guiding tabs 40.

With reference to FIGS. 2 and 4, at least some of the reinforcing ribs 30, especially those which extend parallelly to the rows of openings 20, such as the central reinforcing ribs 310a, 310b, and/or the secondary reinforcing ribs 32, advantageously integrate one guiding tab 40 of the openings 20 between which they extend. As a result, one of the guiding tabs 40 of an opening 20 adjacent to a reinforcing rib 30 may be part of this reinforcing rib 30. These guiding tabs 40 are connected to each other so as to form the corresponding reinforcing rib 30. It should be noted that these guiding tabs 40 forming a reinforcing rib 30 are thicker than the other guiding tabs 40.

The supporting plate 10 advantageously comprises a peripheral edge protruding from one of said upper and lower faces 10a, 10b, for example from the upper face 10a, and surrounding the plurality of openings 20. The peripheral edge and the reinforcing ribs 30 protrude from opposite faces of the supporting plate 10. It should however be noted that the peripheral edge and the reinforcing ribs 30 may protrude from the same face of the supporting plate 10. The peripheral edge advantageously protrude orthogonally to the supporting plate 10.

The peripheral edge extend preferably continuously, i.e. without interruption, all around the supporting plate 10. As shown on the Figures, the peripheral edge may be running on from the peripheral rim.

Preferably, the holding device 1 is made of a plastic material, such as polypropylene (PP). The supporting plate 10, the reinforcing ribs 30 and/or the guiding tabs 40, and/or the peripheral edge are preferably molded in a single piece.

What is claimed is:

1. A holding device configured to support a plurality of medical containers, said holding device comprising:
   a supporting plate, said supporting plate having an upper face, a lower face opposite said upper face, and a plurality of circular openings arranged according to a predetermined pattern and each configured to receive a barrel of one of the medical containers and;
   a plurality of reinforcing ribs protruding from at least one of said upper and lower faces and extending between adjacent circular openings of said plurality of circular openings without intersecting the circular openings,
   wherein the plurality of reinforcing ribs comprises at least one oblique rib extending obliquely relative to a longitudinal direction of the supporting plate from one side to another side of the supporting plate and between two different pairs of adjacent peripheral circular openings, and
   wherein the at least one oblique rib is continuous and non-segmented.

2. The holding device according to claim 1, wherein at least one reinforcing rib extends at least from a row of peripheral openings to another row of peripheral openings.

3. The holding device according to claim 1, wherein the plurality of reinforcing ribs comprises two central ribs intersecting each other substantially at the center of the supporting plate, thereby dividing the supporting plate in four quarters, and four oblique ribs, each extending in one of the four quarters.

4. The holding device according to claim 3, wherein the plurality of reinforcing ribs comprises at least one secondary rib extending parallel to one of said central ribs.

5. The holding device according to claim 4, wherein said at least one secondary rib is orthogonal to a longitudinal direction of the supporting plate.

6. The holding device according to claim 4, wherein said at least one secondary rib is thinner than the central ribs.

7. The holding device according to claim 4, wherein said at least one secondary rib is thinner than the at least one oblique rib.

8. The holding device according to claim 1, wherein the supporting plate comprises a peripheral edge protruding from one of said upper and lower faces and surrounding said plurality of openings.

9. The holding device according to claim 1, wherein at least one of the reinforcing ribs has chamfered ends.

10. The holding device according to claim 1, wherein the at least one oblique rib is straight.

11. The holding device according to claim 1, wherein the at least one oblique rib extends tangentially to the two different pairs of adjacent peripheral circular openings.

12. The holding device according to claim 1, further comprising chimneys surrounding the two different pairs of adjacent peripheral circular openings.

13. An assembly configured to support a plurality of medical containers, the assembly comprising:
    a tub;
    at least one holding device according to claim 1, the at least one holding device being contained inside the tub.

* * * * *